(12) United States Patent
Serman et al.

(10) Patent No.: US 12,702,330 B2
(45) Date of Patent: Aug. 11, 2026

(54) METHOD OF FITTING A HEARING DEVICE AND FITTING DEVICE FOR FITTING THE HEARING DEVICE

(71) Applicant: Sivantos Pte. Ltd., Singapore (SG)

(72) Inventors: Maja Serman, Erlangen (DE); Cecil Wilson, Erlangen (DE)

(73) Assignee: Sivantos Pte. Ltd., Singapore (SG)

( * ) Notice: Subject to any disclaimer, the term of this patent is extended or adjusted under 35 U.S.C. 154(b) by 593 days.

(21) Appl. No.: 18/327,222

(22) Filed: Jun. 1, 2023

(65) Prior Publication Data

US 2023/0389828 A1 Dec. 7, 2023

(30) Foreign Application Priority Data

Jun. 1, 2022 (EP) .................................... 22176842

(51) Int. Cl.
*A61B 5/12* (2006.01)
*H04R 25/00* (2006.01)

(52) U.S. Cl.
CPC ........... *A61B 5/126* (2013.01); *H04R 25/505* (2013.01); *H04R 25/558* (2013.01); *H04R 25/70* (2013.01);

(Continued)

(58) Field of Classification Search
CPC ....... A61B 5/123; A61B 5/126; A61B 5/6815; G06N 3/09; H04R 25/00; H04R 25/30;

(Continued)

(56) References Cited

U.S. PATENT DOCUMENTS 6,700,982 B1 3/2004 Geurts et al.
6,879,693 B2 * 4/2005 Miller .................... H04R 25/70 607/57

(Continued)

FOREIGN PATENT DOCUMENTS

EP 3823306 A1 5/2021
EP 3840222 A1 6/2021
WO 9965276 A1 12/1999

OTHER PUBLICATIONS

Tim Jurgens et al: "Assessment of auditory nonlinearity for listeners with different hearing losses using temporal masking and categorical loudness scaling", Hearing Research, Elsevier Science Publishers, Amsterdam, NL, vol. 280, No. 1, May 18, 2011 (May 18, 2011), pp. 177-191, XP028297018, ISSN: 0378-5955, DOI: 10.1016/J.HEARES.2011.05.016 [retrieved on Jun. 6, 2011] * the whole document *.

(Continued)

*Primary Examiner* — Gerald Gauthier
(74) *Attorney, Agent, or Firm* — Laurence A. Greenberg; Werner H. Stemer; Ralph E. Locher

(57) ABSTRACT

A hearing device has an input transducer, a signal processor for signal amplification and generation of an output signal, and an output transducer for converting the output signal into a sound signal. In a fitting method for fitting the hearing device, at least one test measurement is carried out in which a test signal is generated as an acoustic signal, and in which the hearing device user assesses the resulting sound signal as a test result. A fitting formula is determined based on the test result, and the signal processing device is set based on the fitting formula such that if, during operation of the hearing device, a rise time of a signal start of the input signal is less (Continued)

than or equal to a stored threshold value, then the signal start of the output signal is amplified by a higher gain value than the remaining output signal.

10 Claims, 1 Drawing Sheet

(52) U.S. Cl.
CPC ...... *H04R 2225/61* (2013.01); *H04R 2430/01* (2013.01)

(58) Field of Classification Search
CPC .... H04R 25/305; H04R 25/35; H04R 25/356; H04R 25/50; H04R 25/505; H04R 25/554; H04R 25/558; H04R 25/70; H04R 29/001; H04R 2225/43; H04R 2225/61; H04R 2430/01; H04R 3/04; H04S 7/301; G10K 11/1782; G10L 21/04
See application file for complete search history.

(56) References Cited

U.S. PATENT DOCUMENTS 7,496,205 B2 * 2/2009 Kuhnel .................. H04R 25/70 381/60
7,933,419 B2 * 4/2011 Roeck .................... H04R 25/70 381/314
8,374,877 B2 * 2/2013 Fusakawa ............... G10L 21/04 704/271
8,526,641 B2 * 9/2013 Parker .................... H04R 25/70 607/57
8,553,897 B2 * 10/2013 Anderson ............... H04S 7/301 381/23.1
9,107,016 B2 * 8/2015 Shennib ................. H04R 25/70
9,439,008 B2 * 9/2016 Shennib ................. H04R 25/70
9,491,559 B2 * 11/2016 Anderson ............... H04S 7/301
9,807,522 B2 * 10/2017 Pedersen ................ H04R 25/30
9,918,171 B2 * 3/2018 Shennib ................. H04R 25/70
9,924,284 B2 * 3/2018 Morant ................ H04R 25/554
10,511,921 B2 * 12/2019 Blamey .................. H04R 25/70
11,122,375 B2 * 9/2021 Westergaard ........ H04R 25/554
11,190,883 B2 * 11/2021 Goekay ............ G10K 11/17823
11,558,702 B2 * 1/2023 Hildebrand .......... H04R 25/305
11,671,769 B2 * 6/2023 Lunner .................. H04R 25/70 381/60
12,101,604 B2 * 9/2024 Austin ................. H04R 25/305
2003/0161482 A1 * 8/2003 Miller .................... H04R 25/30 381/60
2003/0163021 A1 * 8/2003 Miller .................... H04R 25/30 600/25
2005/0123145 A1 * 6/2005 Kuhnel .................. H04R 25/70 381/60
2006/0269076 A1 * 11/2006 Miller .................... H04R 25/30 381/60
2007/0076909 A1 * 4/2007 Roeck .................... H04R 25/70 381/60
2011/0004468 A1 1/2011 Fusakawa et al.
2011/0026721 A1 * 2/2011 Parker .................... H04R 25/00 381/59
2013/0208933 A1 * 8/2013 Schmitt .................. H04R 25/50 381/317
2013/0230182 A1 * 9/2013 Hannemann ........... H04R 25/70 381/60
2013/0251165 A1 * 9/2013 Jorgensen ............ H04R 29/001 381/59
2015/0049876 A1 * 2/2015 Kim ....................... H04R 25/70 381/60
2015/0350794 A1 * 12/2015 Pontoppidan ........ A61B 5/6815 381/321
2016/0014532 A1 * 1/2016 Nielsen .................. A61B 5/126 381/60
2016/0324448 A1 * 11/2016 Krueger ................. H04R 25/70
2016/0337769 A1 * 11/2016 Siddhartha ............. H04R 25/70
2017/0238106 A1 * 8/2017 Theill .................... H04R 25/35 381/314
2017/0366904 A1 12/2017 Oetting et al.
2018/0035925 A1 * 2/2018 Boretzki ................ A61B 5/123
2021/0185465 A1 * 6/2021 Bramsløw ................ G06N 3/09
2021/0337301 A1 * 10/2021 Udesen .................... H04R 3/04
2023/0362564 A1 * 11/2023 Serman ................ H04R 25/558
2023/0389828 A1 * 12/2023 Serman ................ H04R 25/558

OTHER PUBLICATIONS

Steffen Kortlang et al: "Auditory Model-Based Dynamic Compression Controlled by Subband Instantaneous Frequency and Speech Presence Probability Estimates", IEEE/ACM Transactions on Audio, Speech, and Language Processing, IEEE, USA, vol. 24, No. 10, Oct. 1, 2016 (Oct. 1, 2016), pp. 1759-1772, XP058327859, ISSN: 2329-9290, DOI: 10.1109/TASLP.2016.2584705, * the whole document *.

Jürgens, Tim et al: "Exploration of a physiologically-inspired hearing-aid algorithm using a computer model mimicking impaired hearing", International Journal of Audiology, vol. 55, No. 6, Jun. 2, 2016 (Jun. 2, 2016), pp. 346-357, XP055577805, UK, ISSN: 1499-2027, DOI: 10.3109/14992027.2015.1135352, * the whole document *.

* cited by examiner

METHOD OF FITTING A HEARING DEVICE AND FITTING DEVICE FOR FITTING THE HEARING DEVICE

CROSS-REFERENCE TO RELATED APPLICATION

This application claims the priority, under 35 U.S.C. § 119, of European Patent Application EP22176842.7, filed Jun. 1, 2022; the prior application is herewith incorporated by reference in its entirety.

FIELD AND BACKGROUND OF THE INVENTION

The invention relates to a method of fitting a hearing device, in particular a hearing aid, and to a corresponding fitting device.

Hearing aids are portable hearing devices (assistive listening devices) that are used to provide hearing to people who are hard of hearing or hearing impaired. In order to meet the numerous individual needs, different designs of hearing aids such as behind-the-ear hearing aids (BTE) and hearing aids with an external receiver (RIC: receiver in the canal) as well as in-the-ear hearing aids (ITE), for example also concha hearing aids or canal hearing aids (ITE: In-The-Ear, CIC: Completely-In-Channel, IIC: Invisible-In-The-Channel) are provided. The hearing devices listed as examples are worn on the outer ear or in the ear canal of a hearing device user. In addition, bone conduction hearing aids, implantable or vibrotactile hearing aids are also available on the market. These stimulate the damaged hearing either mechanically or electrically.

In principle, the primarily important components of such hearing devices are an input transducer, an amplifier, and an output transducer. The input transducer is usually an acousto-electric transducer, such as a microphone, and/or an electromagnetic receiver, for example an induction coil or a (radio frequency, RF) antenna. The output transducer is usually implemented as an electro-acoustic transducer, for example a miniature loudspeaker (earpiece), or an electromechanical transducer, such as a bone conduction earpiece. The amplifier is usually integrated into a signal processing device. The power supply is usually provided by a battery or a rechargeable accumulator.

The input signals received by the input transducers are typically multi-channel, meaning that the input signals are divided into several individual frequency channels, each frequency channel covering a frequency band of a certain spectral width. For example, a hearing aid may have 48 (frequency) channels in a frequency range between 0 Hz (hertz) and 24 kHz (kilohertz), whereby the individual signal components of the input signal in the channels can be individually processed, in particular individually filtered and/or amplified, by means of the signal processing device.

By cleverly adjusting the time-dependent and frequency-dependent amplification or gain of an acoustic input signal by a hearing device, an optimal adaptation to the needs of a hearing device user can be achieved. The problem is to find a rule or an algorithm that can determine an optimal time- and frequency-dependent amplification for any, especially time-variant, speech signal/noise signal mixtures.

For the initial adjustment of the signal amplification and hearing device parameters of the hearing device, so-called fitting formulas are used for this purpose. The aim here is to bring the hearing device settings, in particular the amplification in the individual frequency ranges or frequency channels, as close as possible to the personal or specific requirements of the respective hearing device user.

These fitting formulas or rules may be designed, for example, to improve speech understanding, localisation, sound quality, ambient noise detection or (sound) naturalness. Such fitting formulas may, for example, be linear in order to predict the gain for hearing devices with fixed gain and frequency response curves for the different input levels. Non-linear fitting formulas calculate different gain values depending on the input level and have been developed for hearing aids with wide dynamic range compression (WDRC).

Today, common fitting formulas include NAL-NL-2 and DSLm I/O v5. The fitting formulas take into account not only the gains but also personal and psychoacoustic aspects of the hearing aid user, such as age, gender, experience with hearing aids and speech type. The parameters for the fitting formulas are usually determined from audiometric values during the hearing device fitting using a pure tone audiogram (PTA).

What is commonly referred to as "hearing loss" is actually a series of different pathologies due to the complexity and hierarchical nature of information conversion in a living auditory system. The most prominent deficits that constitute, to a greater or lesser degree, any hearing loss are the loss of hearing threshold (loss of audibility of sounds), the resulting loudness adjustment (loss of normal loudness range), the loss of frequency selectivity, and the loss of temporal resolution.

Because these deficits occur in the same information system, they are interconnected and their behavioral manifestations are difficult to distinguish.

Traditional pure tone audiogram-based hearing device fitting addresses loss of hearing threshold and, to a lesser extent, loss of loudness range, while essentially ignoring loss of frequency selectivity and deficits in temporal processing altogether.

Although compensation of the hearing threshold loss is a necessary prerequisite, this is usually not sufficient to restore normal hearing by means of the hearing device. In addition, broadband amplification is not always beneficial for various hearing disorders and also poses some long-term risks if excessive amplification is used.

In a conventional fitting, frequency-dependent broadband gain is used to compensate for the hearing threshold deficit, and the time constants of an adaptive gain control (AGC) are used to improve the hearing device user's reduced dynamic range. However, neither addresses the spectro-temporal deficits described above.

SUMMARY OF THE INVENTION

It is accordingly an object of the invention to provide a method of fitting a hearing device which overcomes the above-mentioned disadvantages of the heretofore-known devices and methods of this general type and which specifies a particularly suitable method for fitting a hearing device. In particular, the aforementioned shortcomings of traditional, PTA-based broadband gain fitting are to be remedied, and a temporal resolution is to be improved. The invention is further based on the task of specifying a particularly suitable fitting device for carrying out the method.

With the above and other objects in view there is provided, in accordance with the invention, a method of fitting a hearing device, wherein the hearing device includes:

at least one input transducer for receiving an acoustic signal and converting the acoustic signal into an input signal; and a signal processing device for signal amplification of the input signal and generation of an output signal; and an output transducer for converting the output signal into a sound signal; and the method comprises the following steps:

performing at least one test measurement in which a test signal is generated as an acoustic test signal and in which a hearing device user is prompted to judge the acoustic test signal to form a test result;

using the test result to determine a fitting formula; and adjusting the signal processing device with the fitting formula such that, when, in operation of the hearing device, a rise time of a signal start of the input signal is less than or equal to a stored threshold value, the signal processing device causes the signal start of the output signal to be amplified by a higher gain value than a remainder of the output signal.

In other words, the above and other objects are solved with the method as claimed and the fitting device as claimed. Advantageous embodiments and further developments are the subject of the subclaims. The advantages and embodiments cited with regard to the method are also transferable mutatis mutandis to the fitting device and vice versa.

Insofar as process steps are described below, advantageous designs for the adaptation device result in particular from the fact that it is designed to carry out one or more of these process steps.

The method according to the invention is provided for the adaptation or fitting of a hearing device and is suitable and set up for this purpose. The invention is based on the knowledge that the temporal resolution of acoustic signals can be improved by increasing the signal onset. However, the strength and duration of the amplification required for this depend on the hearing loss and are unknown for hearing-impaired persons. In the course of fitting, a fitting formula, or the (input or formula) parameters for it, is therefore determined by means of which the amplification for the beginning and the steady part of a sound signal is adjusted differently during operation of the hearing aid.

The hearing device serves in particular to supply a hearing-impaired user (hearing device user). The hearing device is designed to pick up sound signals from the environment and output them to the hearing device user. For this purpose, the hearing device has at least one input transducer, in particular an acousto-electric transducer, such as a microphone. During operation of the hearing device, the input transducer picks up sound signals (noises, sounds, speech, etc.) from the environment and converts each of these into an electrical input signal. In particular, the input signal is multi-channel. In other words, the acoustic signals are converted into a multi-channel input signal. The input signal thus has several frequency channels, in particular at least two, preferably at least 20, particularly preferably at least 40, for example 48 (frequency) channels, which each cover an associated frequency band of a frequency range of the hearing aid. For example, a frequency range between 0 kHz and 24 kHz is divided into 48 channels, so that input signals with 48 channels are generated.

The hearing device further comprises an output transducer, in particular an electro-acoustic transducer, such as a receiver. An electrical (multi-channel) output signal is generated from the electrical (multi-channel) input signal by modifying (e.g. amplifying, filtering, attenuating) the input signal, or the individual frequency or signal channels, in a signal processing device. The adjustment of the signal processing device, in particular with regard to the signal amplification, is carried out in the course of the fitting using the fitting formula.

According to the method, at least one test measurement is carried out in the course of the fitting, in which a test signal is generated as an acoustic signal, which is converted into a corresponding sound signal by means of the hearing device. In the course of the test measurement, the hearing device user assesses the resulting sound signal, whereby the assessment is stored as a test result.

The test result is used to determine the fitting formula or its parameters. Subsequently, the signal processing device is adjusted on the basis of the fitting formula in such a way that if, during operation of the hearing device, a rise time of a signal start (onset) of the input signal is less than or equal to a stored threshold value, then the signal start of the output signal is amplified by a higher gain value (amplification value) than the remaining output signal. So, a specific onset amplification is generated for the sound signal. Thus, a particularly suitable fitting method is realised, in which an improved temporal resolution of the hearing device is made possible.

In one conceivable embodiment, the fitting formula is estimated or measured from the test result. In other words, a magnitude and duration of the amplification for the beginning and the steady part of the sound signal is estimated or measured for the hearing device user.

Three conceivable methods for determining the adjustment formula are explained in more detail below.

In the first method, the fitting formula or its parameters, in particular the strength and duration of the amplification for the beginning and the steady part of the sound signal, are estimated, whereas in the second and third methods the parameters are measured as test results within the framework of the test measurement.

In the first method, only a pure-tone audiogram is performed as a test measurement and the fitting formula is determined on the basis of the test result. In particular, known fitting formulas are used, which have two versions with different gains. For example, NAL-NI2 is used, which has a fitting formula with less gain for new hearing aid users (e.g. 70% gain) and a fitting formula with more gain for experienced users (e.g. 100% gain).

The hearing device or its signal processing device is set up to recognize the start of hearing or the start of a signal. Determining the signal onset is state of the art (see, e.g., European published patent application EP 3 823 306 A1 and U.S. Pat. No. 6,700,982 B1). Thus, for the first method, the hearing device is arranged to detect a signal onset at an acoustic signal. The threshold value is thus predetermined or pre-characterised by the detection function. The amplification for experienced users is applied to the beginning of the signal, whereas the amplification for new users is used for the rest of the signal. This enables a particularly time- and resource-efficient adaptation of the hearing device.

In the measured second and third method, in an appropriate embodiment for determining the fitting formula, a resolvable time difference for the presentation of test signals and an amplitude difference required to resolve the test signal are respectively determined from the test results. A "resolvable time difference" is understood here and in the following to mean in particular a time difference between two temporally spaced sound signals (tones) at which a hearing device user can still distinguish or separately perceive two successive sound signals or tones. The resolvable time difference is therefore a measure of the temporal resolution. In particular, the resolvable time difference refers to the individual temporal resolution of the hearing aid user, and not to the temporal resolution of the hearing aid. An amplitude difference is understood here and in the following to mean in particular a (individual) level difference between two sound signals (tones) at which the sound signals can be distinguished or perceived separately by the hearing device user, which would be indistinguishable with the same amplitude. The amplitude difference is thus a measure of the gain value. By measuring or determining the time and amplitude difference, a particularly effective and user-specific adaptation of the hearing device can be realised.

In an advantageous further development, the determined time difference is stored and used as a threshold value. In an equally advantageous further development, the gain value is determined using the amplitude difference. This ensures a particularly suitable and reliable adjustment of the hearing device.

In a preferred embodiment, a twin tone, i.e., two tones of the same frequency, which are temporally spaced and/or have different signal levels/amplitudes, is used as the test signal. By changing the temporal distance and/or the signal amplitudes, a reliable and simple determination of the time difference and/or the amplitude difference is possible. The conjunction "and/or" is to be understood here and in the following in such a way that the features linked by means of this conjunction can be designed both together and as alternatives to each other.

For the second method, the fitting formula is measured based on a pure tone audiogram, a gap detection (time) and just perceptible level differences (amplitude). In a suitable embodiment, the time difference is determined here by means of a gap detection measurement and the amplitude difference by means of a level difference measurement. The gap detection measurement (in quiet and in noise) is performed at different frequencies to determine a time difference for the different frequency channels (dT(f)). The just perceptible level difference is measured at audiogram frequencies in addition to the hearing threshold to determine a value for the amplitude difference (dA(f)).

For the third method, alternatively, the fitting formula, in particular the time difference and the amplitude difference, is determined on the basis of a combined time-amplitude measurement. In the combined time-amplitude measurement, essentially two test measurements are performed. First, a multi-tone measurement, in particular a twin-tone measurement, is used as the first test measurement, whereby two time-separated sound signals are generated as the test signal, and whereby the time interval between the sound signals is successively or iteratively reduced until the hearing device user perceives only a single tone in the generated sound signal. The corresponding time interval between the sound signals, i.e. the time difference at which it is no longer possible to distinguish between the individual signals, is determined as the test result. In a subsequent second test measurement, the amplitude, i.e. the signal level, for one of the sound signals is successively or iteratively increased until the hearing device user again perceives two distinguishable sounds in the generated sound signal. The amplitude difference or the amplitude difference between the two sound signals at which the discriminability occurs again is determined as the test result. The test measurements are performed repeatedly for different frequencies. In particular, the test measurements are performed for each frequency channel of the hearing aid.

To measure the temporal aspects, a multi-tone presentation is thus used, in which for a series of frequencies, for example, two temporally separated tone signals (twin tone) are presented one after the other. The initial presentation level of the first tone is based on a pure tone audiogram (frequency specific). The level or amplitude difference between the first tone signal and the second tone signal can be determined in the first iteration. The time interval between the sound signals decreases over the course of the subsequent presentation, with the hearing device user being asked after each presentation whether they can hear only one sound signal or multiple sound signals in the generated sound signal. Once the hearing device user indicates that only one sound is presented, the sound presentation sequence is stopped and a change to an amplitude sweep or sampling is made.

In amplitude sweep, for example, the amplitude of the second audio signal is increased at each presentation. The initial time difference between the first and second sound signals may be less than or equal to the resolvable time difference found or determined in multi-tone presentation. When the hearing device user perceives only one sound signal, the volume of the second sound signal is increased. This is repeated until the hearing device user again detects two separately perceivable sound signals in the generated sound signal. The amplitude difference at which the two sound signals are again detected is defined as a measure of the onset gain required for that subject at that frequency (gain value). The entire process is repeated for the next frequency until all relevant frequency points or frequency channels have been processed.

Two result measures are thus derived from the combined time-amplitude measurement. On the one hand, the resolvable time difference for the presentation of twin tones, and on the other hand, the amplitude difference required to resolve the twin tone that is presented at the moment that is still perceptible.

If the rise time is faster/smaller than the just perceptible gap difference dT(f), then according to the invention an amplification of the signal start or signal onset is provided. The required onset amplification is then calculated on the basis of the derived amplitude difference dA(f). In a suitable design, the gain value oG(f) at a frequency or for a frequency channel f is calculated using the formula $$oG(f)=dA(f)\times[\max(\{dT(f)-t\mathrm{rise}(f)\},0)+t\mathrm{offset}(f))]\times a\mathrm{offset}(f)$$

where dA(f) is the amplitude difference and dT(f) the time difference and trise(f) the rise time of the input signal. The constants or offsets for the time component toffset(f) and the amplitude component aoffset(f) are determined, for example, by means of an optimization. Alternatively, the offset values toffset(f) and aoffset(f) can be stored values, which can be research or evidence based.

If the time difference is greater than the rise time (dT(f) >trise(f)), the onset increase of dA(f) shall be applied, this effectively corresponds to the threshold comparison. Then the expression max({dT(f)−trise(f)}, 0) is a positive number, and correspondingly oG(f) will also be a positive number based on the offset values toffset(f) and aoffset(f). The constants toffset(f) and aoffset(f) help scale and offset the applied amplitude difference dA(f). The constants toffset(f) and aoffset(f) are preferably predetermined and stored on the basis of corresponding experiments.

An additional or further aspect of the invention provides a fitting device for fitting a hearing device. In this aspect, the fitting device comprises a test means for performing test measurements, whereby at least one test result is obtained, and an adjustment means for adjusting the hearing device with a fitting formula, as well as a controller (i.e., a control unit) for performing a method described above.

In this case, the controller is generally set up—in terms of programming and/or circuitry—to carry out the method according to the invention described above. The controller is thus specifically set up to generate an adjustment formula for the adjustment device on the basis of the test result. The adjustment formula is designed in such a way that if, during operation of the hearing device, a rise time of a signal start of an input signal is less than or equal to a stored threshold value, then a signal start of an output signal is amplified by a higher amplification value than the remaining output signal.

In a preferred embodiment, the controller is formed, at least in its core, by a microcontroller with a processor and a data memory in which the functionality for carrying out the method according to the invention is implemented programmatically in the form of operating software (firmware), so that the method is carried out automatically—if necessary in interaction with a device user—when the operating software is executed in the microcontroller. Alternatively, within the scope of the invention, the controller can also be formed by a non-programmable electronic component, such as, for example, an application-specific integrated circuit (ASIC) or by an FPGA (field programmable gate array), in which the functionality for carrying out the method according to the invention is implemented by circuit-technical means.

The determination of the fitting formula can be based on a conventional PTA-based fitting formula, for example. Alternatively, the fitting formula can be determined based on a gap detection (temporal) and JND (just noticeable difference) loudness difference at threshold (amplitude measurement). Further, alternatively, a fitting formula based on a measurement of a time-amplitude response is also possible.

Other features which are considered as characteristic for the invention are set forth in the appended claims.

Although the invention is illustrated and described herein as embodied in a method of fitting a hearing device and a fitting device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE FIGURES

Corresponding parts and sizes are provided with the same reference signs throughout the figures.

DETAILED DESCRIPTION OF THE INVENTION

Figure 1:
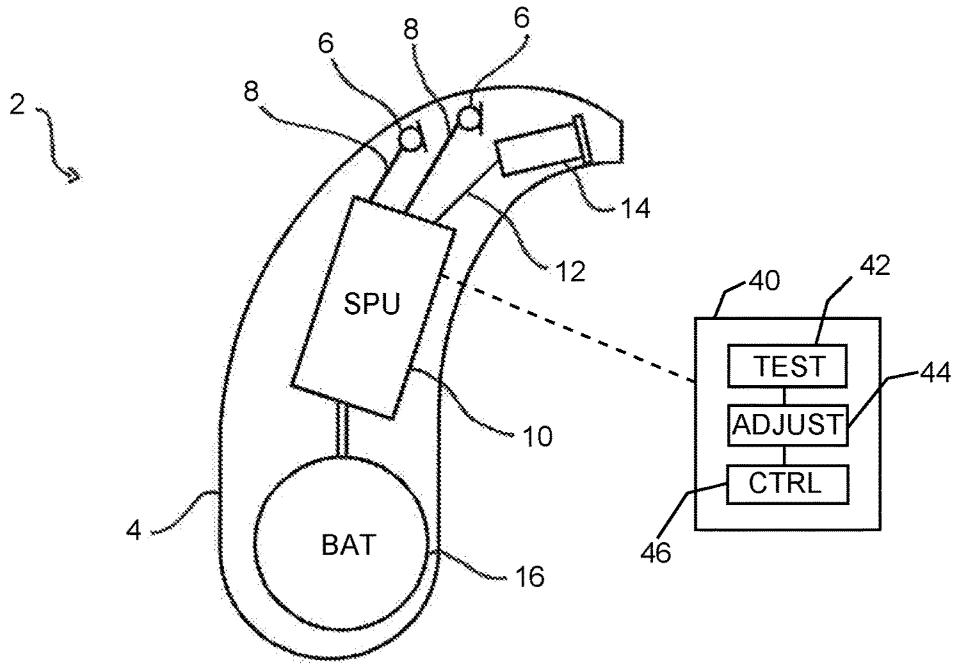
FIG. 1 is a diagrammatic view of a hearing device.

Referring now to the figures of the drawing in detail and first, in particular, to FIG. 1 thereof, there is shown a basic design of a hearing device 2. The exemplary hearing device 2 is designed as a behind-the-ear hearing aid (BTE).

As shown schematically in FIG. 1, the hearing device 2 comprises a device housing 4 in which one or more microphones, also referred to as (acousto-electric) input transducers 6, are installed. The input transducers 6 are used to pick up a sound or the acoustic signals in an environment of the hearing device 2 and to convert them into electrical, multichannel, input signals 8. Preferably, the input signals 8 have several frequency channels, for example 48 channels in the frequency range between 0 kHz and 28 kHz.

A signal processing unit 10, which is also integrated in the device housing 4, processes the input signals 8. An output signal 12 of the signal processing unit 10 is transmitted to an output transducer 14, which is designed, for example, as a loudspeaker or earpiece, which outputs an acoustic signal. In the case of the hearing device 2, the acoustic signal is transmitted to the eardrum of a hearing system user, if necessary, via a sound tube or external earpiece not shown in more detail, which is fitted with an earmold that sits in the auditory canal. However, an electro-mechanical output transducer 14 is also conceivable as a receiver, as in the case of a bone conduction receiver, for example.

The power supply of the hearing device 2 and in particular that of the signal processing device 10 is provided by a battery 16 that is also integrated in the device housing 4.

A method for fitting the hearing device 2 is carried out, for example, by way of a fitting device 40 which can be connected to the hearing device 2 by way of a signal connection. The fitting device 20, by way of example, includes a test device 42, an adjustment device 44 by way which the signal processor 10 of the hearing device is adjusted, and a controller 46.

Figure 2:
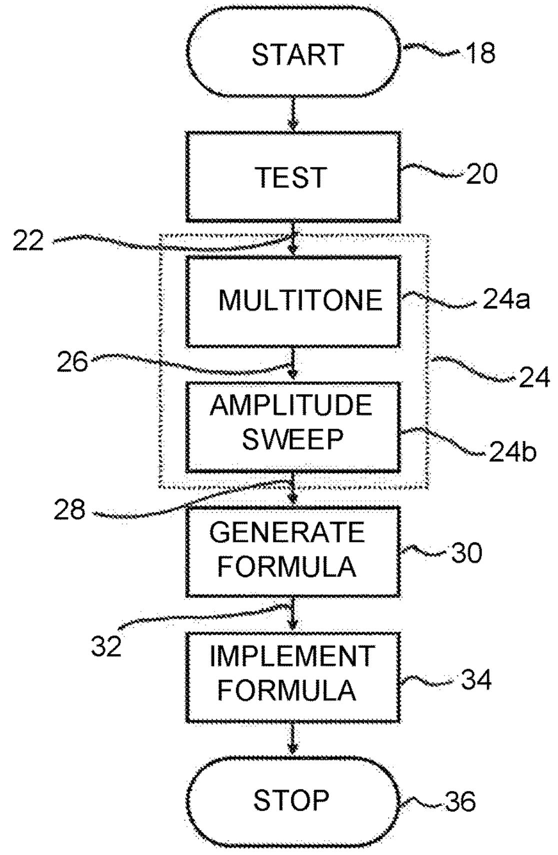
FIG. 2 a flow diagram for a method of fitting the hearing device.

Referring now to FIG. 2, in the course of the procedure, the settings and parameters of the hearing device 2 or the signal processing device 10 are adapted to the needs of a hearing device user.

In the exemplary embodiment shown, test measurements are carried out after a process start 18, in each of which a test signal is generated as an acoustic signal, which is converted by means of the hearing device 2 into a corresponding sound signal for the hearing device user, whereby the hearing device user assesses the generated sound signal within the framework of the respective test measurement. The result is stored as a test result and used for further fitting.

After the process start 18, a pure tone audiogram is first performed as a test measurement 20, by means of which a loss of the hearing threshold and, to a lesser extent, a loss of the volume range of the hearing device user is detected. A test result 22 of the test measurement 20 is used for a subsequent test measurement 24.

The test measurement 24 is designed as a combined time-amplitude measurement and essentially has two successive (partial) test measurements 24*a*, 24*b*.

In the first test measurement 24*a*, deficits in the temporal processing or temporal resolution of the hearing device user are determined. For the measurement of the temporal aspects, a multi-tone presentation, in particular a twin-tone presentation, is used, in which two temporally separated sound signals (twin tone) are presented as testsignal one after the other for a series of frequencies. The initial presentation level (signal volume) of the first tone is based on the test result 22 of the pure tone audiogram (frequency-specific). The level or amplitude difference between the first tone signal and the second tone signal can be determined in the first iteration. The time interval between the sound signals decreases over the course of the subsequent presentation, with the hearing device user being asked after each presentation whether they can hear only one sound signal or multiple sound signals in the generated sound signal. Once the hearing device user indicates that only one tone is presented, the resolvable time difference for the presentation of the twin tones is stored as test result 26. Subsequently, the tone presentation sequence of test measurement 24*a* is stopped and a change is made to an amplitude sweep or amplitude sampling of test measurement 24*b*.

For example, in the amplitude sampling of the test measurement 24*b*, the amplitude of the second audio signal is increased at each presentation. The initial time difference between the first and second audio signals may be less than or equal to the resolvable time difference (test result 26) determined in test measurement 24*a*. If the hearing device user perceives only one sound signal, the volume of the second sound signal is increased. This is repeated until the hearing device user again detects two separately perceivable sound signals in the generated sound signal. The amplitude difference at which two sound signals are again detected is stored as test result 28. The test result 28 is a measure of the onset gain required for the hearing device user 2 at this frequency (gain value). The entire process is repeated for the next frequency until all relevant frequency points or frequency channels have been processed.

The combined time-amplitude measurement 24 thus provides a test result 28 with two outcome measures. On the one hand, the resolvable time difference (gap difference) for the presentation of twin tones, and on the other hand, the amplitude difference required to resolve the twin tone presented at the just perceptible time.

A fitting formula 32 is then determined from the test result 28 in a process step 30. The fitting formula 32 is designed in such a way that it implements an onset amplification in the hearing device 2 or in the signal processing device 10 to improve the spectro-temporal deficits of the hearing device user. For this purpose, the rise time or the rise rate of an input signal 8 is detected during operation of the hearing device 2. If the rise time is faster/smaller than the just perceivable gap difference or time difference (test result 26), then an increased amplification of the signal onset or signal onset occurs. The required onset gain or gain value is then calculated based on the derived amplitude difference (test result 28).

The gain value oG(f) at a frequency or for a frequency channel f is calculated with the formula $$oG(f)=dA(f)\times[\max(\{dT(f)-t\mathrm{rise}(f)\},0)+t\mathrm{offset}(f))]\times a\mathrm{offset}(f)$$

where dA(f) is the amplitude difference and dT(f) the time difference and trise(f) the rise time of the input signal. The constants or offsets for the time component toffset(f) and the amplitude component aoffset(f) are determined by means of an optimization.

In a process step 34, the fitting formula 32 is transferred to the hearing device 2 or to the signal processing device 10. The hearing device 2 is thus adjusted using the fitting formula 32. Here, the above formula for calculating the gain value is stored together with the parameters dA(f), dT(f), toffset(f), and aoffset(f) in a memory of the signal processing device 10, which determines the rise time trise(f) during operation of the hearing device 2, and calculates and sets the gain value oG(f) for the onset gain using the formula.

After the adjustment of the hearing device 2, the method is terminated in a process step 36.

It will be understood that the claimed invention is not limited to the exemplary embodiment described above. Rather, other variants of the invention may also be derived therefrom by the skilled person within the scope of the disclosed claims without departing from the subject-matter of the claimed invention. In particular, all individual features described in connection with the embodiment example can also be combined in other ways within the scope of the disclosed claims without departing from the subject-matter of the claimed invention.

In particular, instead of the combined time-amplitude measurement 24, a gap detection (temporal) and JND (just noticeable difference) loudness difference at threshold (amplitude measurement) can also be performed. Furthermore, for example, the determination of the fitting formula based on a conventional, PTA-based fitting formula, such as NAL-NL-2.

The following is a summary list of reference numerals and the corresponding structure used in the above description of the invention:

2 Hearing device
4 Device housing
6 Input transducer
8 Input signal
10 Signal processing device (SPU)
12 Output signal
14 Output transducer
16 Battery (BAT)
18 Process start
20 Test measurement/pure tone audiogram
22 Test result
24 Test measurement/time amplitude measurement
24*a* Test measurement/multi-tone presentation
24*b* Test measurement/amplitude sweep
26 Test result
28 Test result
30 Process step
32 Fitting formula
34 Process step
36 Process end
40 Fitting device
42 Test device
44 Adjustment device
46 Controller

The invention claimed is:

1. A method of fitting a hearing device, wherein:

the hearing device comprises:

a) at least one input transducer for receiving an acoustic signal and converting the acoustic signal into an input signal; and b) a signal processing device for signal amplification of the input signal and generation of an output signal; and c) an output transducer for converting the output signal into a sound signal; and the method comprises:

performing at least one test measurement in which a test signal is generated as an acoustic test signal and in which a hearing device user is prompted to judge the acoustic test signal to form a test result;

using the test result to determine a fitting formula; and adjusting the signal processing device with the fitting formula such that, when, in operation of the hearing device, a rise time of a signal start of the input signal is less than or equal to a stored threshold value, the signal processing device causes the signal start of the output signal to be amplified by a higher gain value than a remainder of the output signal.

2. The method according to claim 1, wherein the fitting formula is an estimated formula or a measured formula.

3. The method according to claim 1, wherein the step of determining the fitting formula comprises determining a resolvable time difference for a presentation of test signals and an amplitude difference required to resolve the test signal.

4. The method according to claim 3, which comprises storing the time difference and using the time difference as a threshold value.

5. The method according to claim 3, which comprises determining a gain value on a basis of the amplitude difference.

6. The method according to claim 3, which comprises using a twin tone as the acoustic test signal.

7. The method according to claim 3, which comprises determining the time difference by way of a gap detection measurement and determining the amplitude difference by way of a level difference measurement.

8. The method according to claim 3, which comprises determining the time difference and the amplitude difference by way of a combined time-amplitude measurement in which:

a multi-tone measurement is used in a first test measurement, wherein two temporally separated sound signals are generated as a test signal, and wherein the temporal distance between the sound signals is iteratively reduced until the hearing device user perceives only one tone in the generated sound signal;

in a subsequent second test measurement the amplitude of one of the sound signals is successively increased until the hearing device user perceives two sounds in the generated sound signal; and the first and second test measurements are repeated for different frequencies.

9. The method according to claim 3, which comprises calculating the gain value with the formula $$oG(f)=dA(f)\times[\max(\{dT(f)-t\text{rise}(f)\},0)+t\text{offset}(f))]\times a\text{offset}(f)$$

wherein:

oG(f) is the gain value is the amplitude difference, dT(f) is the time difference, trise(f) is the rise time of the input signal, and toffset(f) and aoffset(f) are optimization constants.

10. A fitting device for fitting a hearing device, the fitting device comprising:

a test device for carrying out test measurements to obtain at least one test result;

an adjustment device for adjusting the hearing device with a fitting formula; and a controller for carrying out the method according to claim 1.

* * * * *